(12) United States Patent
Chiang

(10) Patent No.: US 7,257,848 B2
(45) Date of Patent: Aug. 21, 2007

(54) SWIMMING GOGGLES

(76) Inventor: Herman Chiang, 11F-2 No. 634-9 Ching-Ping Rd., Chung-Ho City, Taipei Hsien (TW)

( * ) Notice: Subject to any disclaimer, the term of this patent is extended or adjusted under 35 U.S.C. 154(b) by 213 days.

(21) Appl. No.: 11/092,929

(22) Filed: Mar. 30, 2005

(65) Prior Publication Data
US 2006/0218705 A1 Oct. 5, 2006

(51) Int. Cl.
*A61F 9/02* (2006.01)
(52) U.S. Cl. .............................................. 2/448; 2/450
(58) Field of Classification Search .................... 2/426, 2/428, 440, 442, 445, 448, 450; 351/43
See application file for complete search history.

(56) References Cited
U.S. PATENT DOCUMENTS

| | | | |
|---|---|---|---|
| 6,276,795 B1 * | 8/2001 | Hall et al. ..................... 351/62 |
| 6,349,419 B1 * | 2/2002 | Chiang ........................... 2/428 |
| 6,349,420 B1 * | 2/2002 | Chiang ........................... 2/428 |
| 6,832,394 B1 * | 12/2004 | Chiang ........................... 2/428 |
| 7,007,311 B2 * | 3/2006 | Chiang ........................... 2/448 |
| 7,020,905 B2 * | 4/2006 | Chiang ........................... 2/448 |
| 7,055,182 B2 * | 6/2006 | Chiang ........................... 2/450 |
| 7,134,148 B2 * | 11/2006 | Shiue ............................. 2/428 |
| 7,146,654 B2 * | 12/2006 | Chiang ........................... 2/428 |

* cited by examiner

*Primary Examiner*—Katherine Moran
(74) *Attorney, Agent, or Firm*—Troxell Law Office, PLLC

(57) ABSTRACT

Swimming goggles comprise a frame, eyeglasses, a pad and compressing devices. The eyeglasses are received in the pad, and the compressing devices are mounted on opposite outer sides of the frame for compressing the eyeglasses and the pad, wherein each compressing device includes a first cover and a second cover which are assembled together and receive a head strip. The frame has an upper frame, a lower frame and a nose support. Cracks are defined on both sides of the upper frame and the lower frame. The upper frame forms a gap in a middle of an inner edge thereof for making the frame flexible to bend inwardly thereby fitting for various users who have different face profiles.

13 Claims, 5 Drawing Sheets

SWIMMING GOGGLES

BACKGROUND OF THE INVENTION

1. Field of the Invention

The present invention relates to swimming goggles, and particularly to swimming goggles which have a frame compressing eyeglasses and a pad together and which are flexible to make users feel comfortable and prevent from leakage.

2. Related Art

Conventional swimming goggles 9, which have a frame 90 compressing eyeglasses 91 and a pad 92 together, are illustrated in FIG. 6. The eyeglasses 91 and the pad 92 are both assembled on predetermined holes 901 of the frame 90. Connectors 93 press upon opposite sides of the frame 90 to compress the eyeglasses 91 and the pad 92 together.

However, the frame 90 is not flexible enough to bend inwardly owing to hard upper portion 902 of the frame 90. Correspondingly, users, who have small face profiles, will feel uncomfortable due to unsuitable touch. At the same time, the frame 90 of the conventional swimming goggles 9 tends to leak. In addition, side portions 941 of the frame 90 under a nose support 94 touch faces of users directly, resulting in uncomfortable feeling because the frame 90 is made of hard material.

SUMMARY OF THE INVENTION

Accordingly, an object of the present invention is to provide swimming goggles which serve users well and prevent from water leakage as wearing. The swimming goggles comprise a frame which has flexible an upper portion to bend inwardly for fitting for various face profiles of uses. Additionally, the frame has a lower portion shrouded of soft material for providing users with further comfortable feeling.

The swimming goggles have a frame compressing eyeglasses and a pad together. The frame has an upper frame, a lower frame and a nose support. The upper frame forms a gap in a middle of an inner edge thereof, whereby the frame is flexible enough to bend inwardly freely.

DESCRIPTION OF THE PREFERRED EMBODIMENTS

Figure 1:
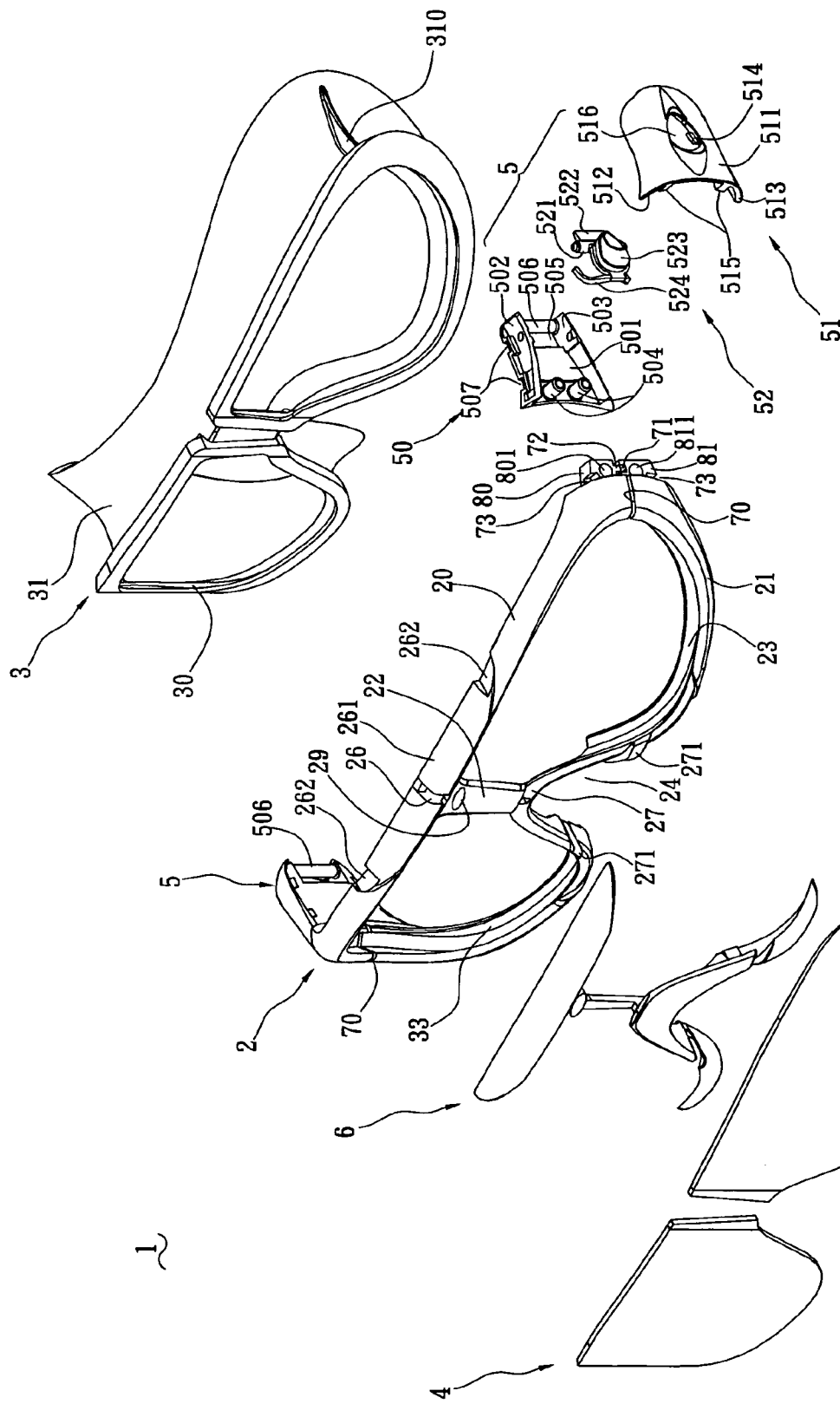
FIG. 1 is a perspective exploded view of swimming goggles of the present invention.
Figure 1A:
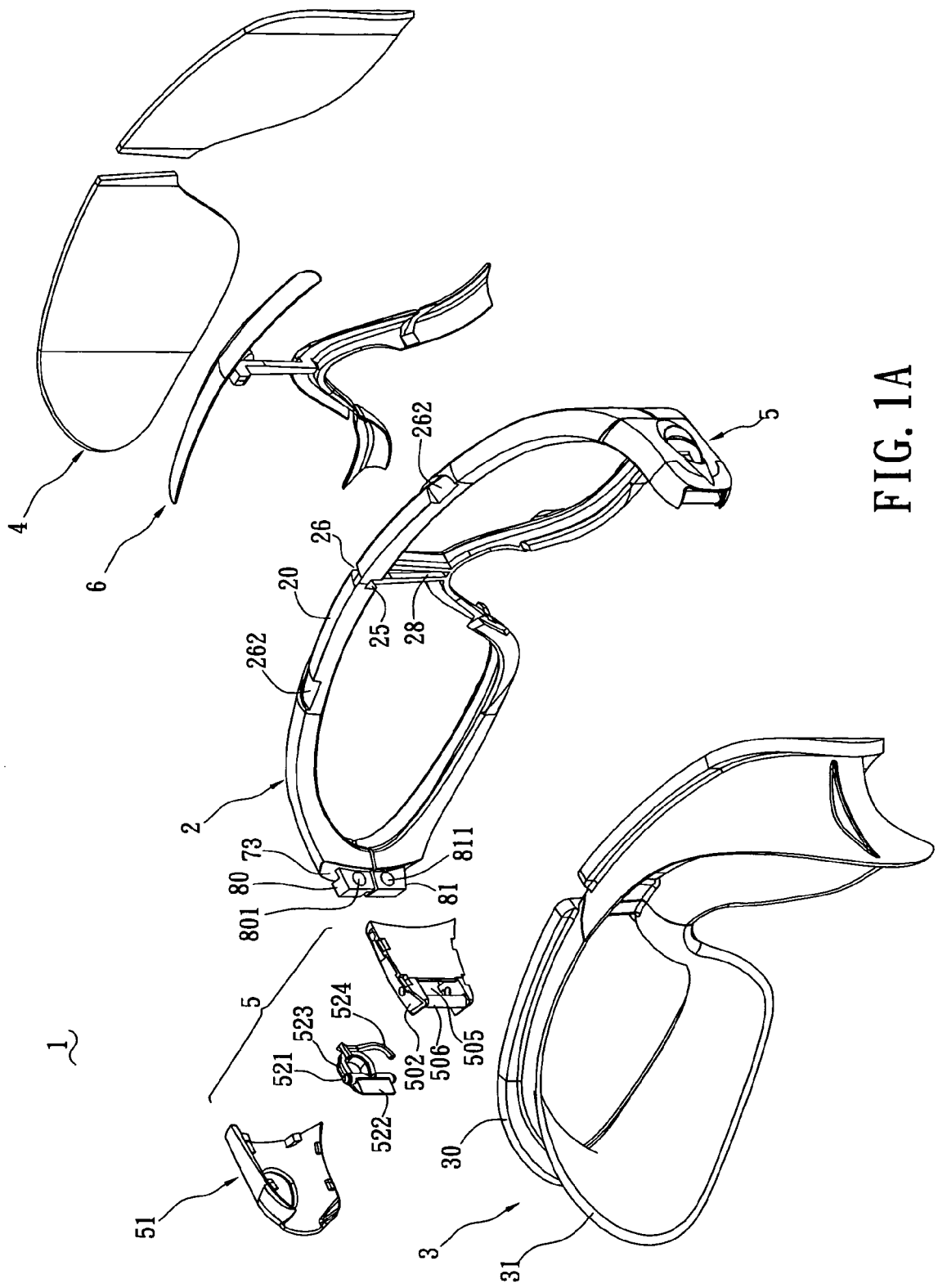
FIG. 1A is another exploded view of swimming goggles of FIG. 1.
Figures 3, 4:
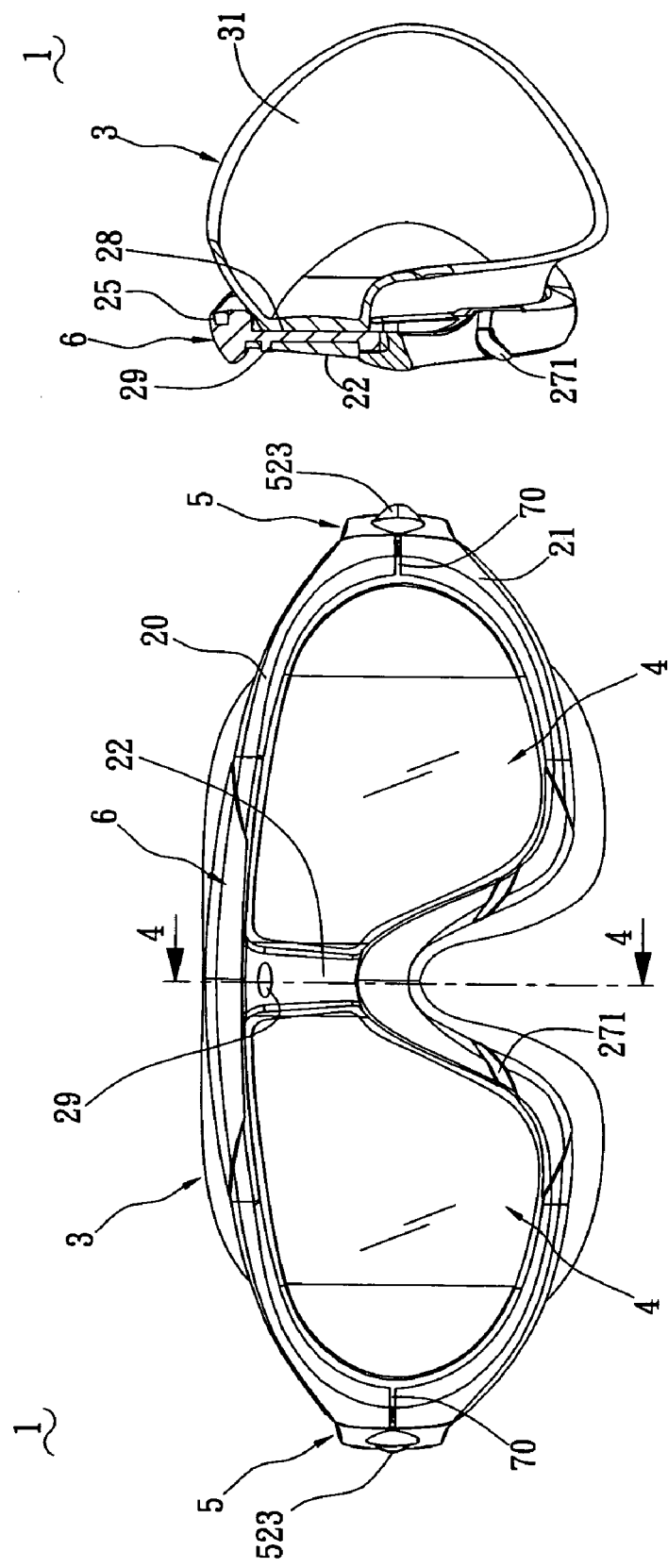
FIG. 3 is a front view of the swimming goggles of FIG. 2.
FIG. 4 is a cross-sectional view taken along the line 4-4 in FIG. 3.
Figure 6:
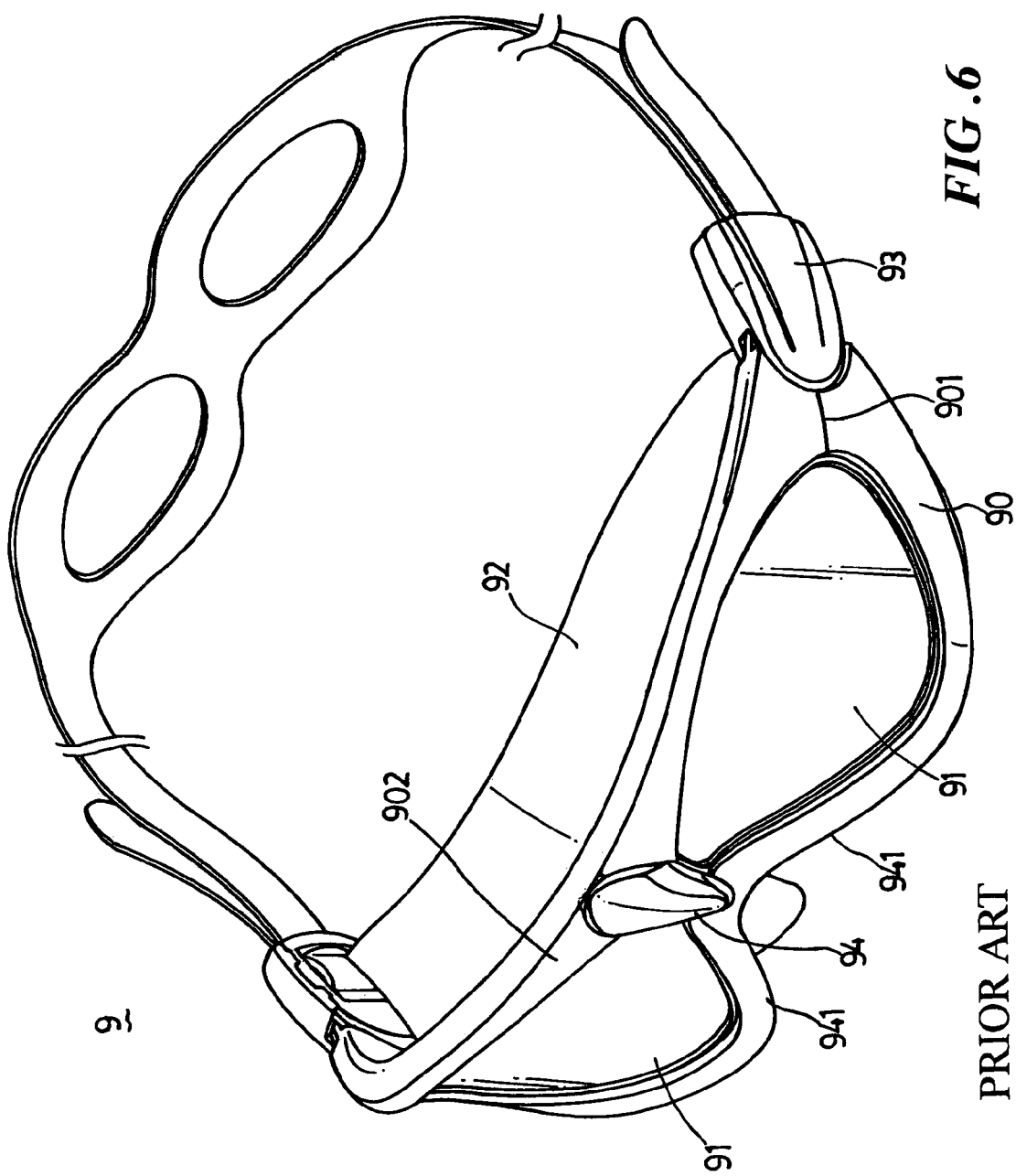
FIG. 6 is a perspective view of conventional swimming goggles.

With reference to FIG. 1, swimming goggles 1 of the present invention comprise a frame 2, a pad 3, two eyeglasses 4 and compressing devices 5. The frame 2 has an upper frame 20, a lower frame 21 and a nose support 22. The upper frame 20 and the lower frame 21 define closed space for accommodating the eyeglasses 4. Receiving grooves 23, 33 are respectively defined along inner edges of the upper frame 20 and the lower frame 21 for receiving the pad 3. The nose support 22 is arranged on a middle of the upper frame 20, and connects the upper frame 20 and the lower frame 21 thereby dividing the closed space into two slots (not labeled) respectively for accommodating the eyeglasses 4. The lower frame 21 forms a concave portion 24 for straddling a user's nose. The upper frame 20 forms a gap 25 (shown in FIG. 1A) in a middle of an inner edge thereof, and forms an inject hole 26 communicating with the gap 25. Camber portions 261 are slightly concave respectively on both sides of the inject hole 26. Engaging grooves 262 are respectively formed on both sides of the camber portions 261, whereby the soft frame 6 covers the inject hole 26 and the camber portions 261 and clamps the engaging grooves 262. The lower frame 21 has an enveloping surface 27 about the concave portions 24. Similarly, the enveloping surface 27 is shrouded by the soft frame 6, whereby the portions about the concave portions 24 are of comfortable touch. Barbs 271 are provided on the enveloping surface 27 for retaining the soft frame 6. Further referring to FIG. 4, an enveloping groove 28 is defined in the nose support 22 and communicates with the gap 25. A mark hole 29 is defined in the nose support 22 and communicates with the enveloping groove 28. The mark hole 29 may be shaped as characters or pictures of a brand mark. The soft frame 6 also shrouds the enveloping groove 28 and the mark hole 29. During manufacturing, soft material is injected into the injecting hole 26, the camber portions 261, the engaging grooves 262, the gap 25, the enveloping groove 28 and the mark hole 29, forming the soft frame 6.

Referring to FIG. 1, cracks 70 are defined on both sides of the upper frame 20 and the lower frame 21 for mounting the pad 3 and the eyeglasses 4 thereon. A first connecting base 80 and a second connecting base 81 unitarily extend from the upper frame 20 and the lower frame 21 and are respectively distributed on opposite sides of the cracks 70. Connectors, for example apertures 801, 811, are respectively defined in the first connecting base 80 and the second connecting base 81. Positioning grooves 71 and positioning projections 72 are respectively formed near the cracks 70 for positioning the engagement of the first connecting base 80 and the second connecting base 81. Latch grooves 73 are formed on upper of lateral sides of the first connecting base 80 and the second connecting base 81 for latching the compressing devices 5.

The pad 3 comprises an eyeglasses portion 30 and a touch portion 31. The eyeglasses portion 30 receives eyeglasses 4 and is sandwiched in the receiving grooves 23, 33. The touch portion 31 extends unitarily and inwardly from the eyeglasses portion 30 for completely covering a user's face. Enhancing ribs 310 are formed on outer sides of the touch portion 31.

The compressing devices 5 are mounted on opposite outer sides of the frame 2. Each compressing device 5 comprises a first cover 50 and a second cover 51 which are assembled together, and a head-strip lock 52 for retaining the head strip (not shown). The first cover 50 includes a first bottom wall 501 and opposing first sidewalls 502, 503. An engaging block, for example a cylinder 504, is formed on an edge of the first bottom wall 501 for engaging with the apertures 801, 802 of the first connecting base 80 and the second connecting base 81. An opening 505 is defined in an edge of the first bottom wall 501 and opposite to the engaging block 504. A guiding post 506 is formed between the first sidewalls 502, 503 to retain a head strip (not shown). First lock portions, for example locking grooves 507, are respectively defined on bottoms of the first sidewalls 502, 503. The first sidewalls 502, 503 respectively define axis holes 508 therein.

The second cover 51 has a second bottom wall 511 and opposing second sidewalls 512, 513. Second lock portions, for example protuberances 514, are formed on the second bottom wall 511 for cooperating with the locking grooves 507 to assemble the first cover 50 and the second cover 51 together. Latching posts 515 are formed on a forward edge of the second bottom wall 511 for locking the latch grooves 73 of the first connecting base 80 and the second connecting base 81.

The head-strip lock 52 is assembled as a lever on opposite sides of the first cover 50, and comprises a fixing pole 521, stop strips 522 on both sides of the fixing lever 521, and a button 523. The fixing pole 521 is assembled as a level on axis holes 508 of the first cover 50. The stop strips 522 extend from an end of the fixing pole 521 and near the opening 505 of the first cover 50, allowing the head strip (not shown) to move in a single direction. The button 523 extends from another end of the fixing pole 521 and opposite the stop strips 522. In assembly, an upper portion of the button 523 extends beyond an assembling hole 516 of the second cover 51. A resilient pole 524 is formed on the second cover 52 for providing return force of the button 523. In normal state, the resilient pole 524 biases the button 523 upwardly, and the stop strips 522 biases against positioning holes of the head strip (not shown); when the button 523 is pressed downwardly, the stop strips 522 move upwardly thereby allowing the head strip to move in bi-directions; when the button 523 is put to be free, the resilient pole 524 drives the button 523 to return and biases the button 523 upwardly again.

Figure 2:
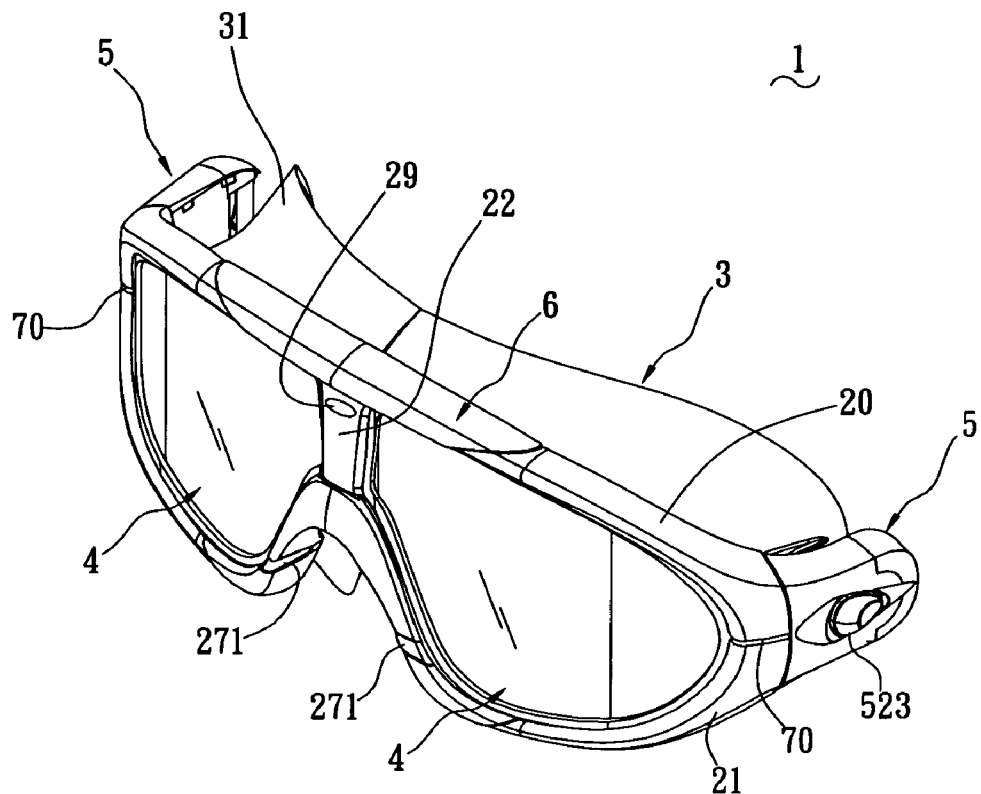
FIG. 2 is an assembled view of the swimming goggles of FIG. 1.
Figure 5:
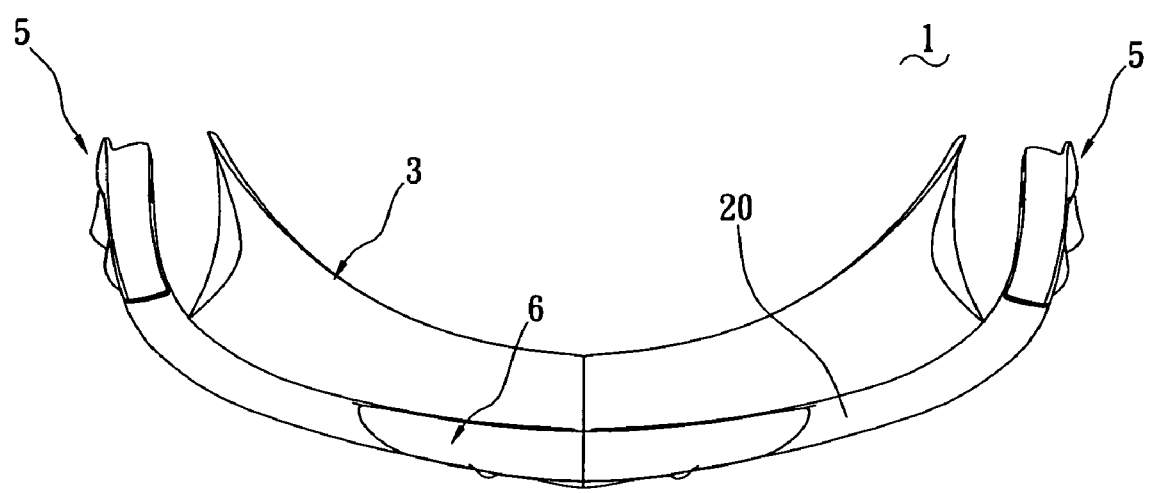
FIG. 5 is a top view of FIG. 2.

Combining with FIGS. 1, 2 and 5, the frame 2 is made of hard material. The soft frame 6 injects to the frame 2, and shrouds the concave portions 24, and the gap 25 on the upper frame 20. Thus, the upper frame 20 is flexible enough to bend inwardly freely thereby fitting for users who have different face profiles and preventing from leakage as wearing.

It is understood that the invention may be embodied in other forms without departing from the spirit thereof. Thus, the present examples and embodiments are to be considered in all respects as illustrative and not restrictive, and the invention is not to be limited to the details given herein.

The invention claimed is:

1. Swimming goggles comprising:
   a casing frame including an upper frame, a lower frame and a nose support, the upper frame and the lower frame defining closed space, receiving grooves being respectively defined along inner edges of the upper frame and the lower frame for receiving the pad, cracks being defined on both sides of the upper frame and the lower frame, the nose support being arranged on a middle of the upper frame and connecting the upper frame and the lower frame thereby dividing the closed space into two slots, the lower frame forming a concave portion, the upper frame forming a gap in a middle of an inner edge thereof;
   a pad including an eyeglasses portion and a touch portion, the eyeglasses portion being sandwiched in the receiving grooves;
   eyeglasses received in the eyeglasses portion of the pad; and
   compressing devices mounted on opposite outer sides of the casing frame, each compressing device including a first cover and a second cover which are assembled together and receive a head strip,
   wherein an enveloping groove is defined in the nose support and is shrouded with soft material.

2. The swimming goggles as claimed in claim 1, wherein touch portion of the pad extends unitarily and inwardly from the eyeglasses portion for completely covering a user's face, enhancing ribs being formed on outer sides of the touch portion.

3. The swimming goggles as claimed in claim 1, wherein the nose support further has a mark hole which communicates with the enveloping groove and is shrouded with soft material.

4. The swimming goggles as claimed in claim 3, wherein the mark hole is shaped as characters or pictures of a brand mark.

5. The swimming goggles as claimed in claim 4, wherein the lower frame has an enveloping surface about the concave portions, and the enveloping surface is shrouded by soft material, whereby the portions about the concave portions are of comfortable touch.

6. The swimming goggles as claimed in claim 5, wherein barbs are provided on the enveloping surface for retaining the soft material.

7. Swimming goggles comprising:
   a casing frame including an upper frame, a lower frame and a nose support, the upper frame and the lower frame defining closed space, receiving grooves being respectively defined along inner edges of the upper frame and the lower frame for receiving the pad, cracks being defined on both sides of the upper frame and the lower frame, the nose support being arranged on a middle of the upper frame and connecting the upper frame and the lower frame thereby dividing the closed space into two slots, the lower frame forming a concave portion, the upper frame forming a gap in a middle of an inner edge thereof;
   a pad including an eyeglasses portion and a touch portion, the eyeglasses portion being sandwiched in the receiving grooves;
   eyeglasses received in the eyeglasses portion of the pad; and
   compressing devices mounted on opposite outer sides of the casing frame, each compressing device including a first cover and a second cover which are assembled together and receive a head strip,
   wherein a first connecting base and a second connecting base unitarily extend from the upper frame and the lower frame and are respectively distributed on opposite sides of the cracks, and wherein connectors are respectively defined in the first connecting base and the second connecting base, and the connectors are through holes.

8. The swimming goggles as claimed in claim 7, wherein latch grooves are formed on upper of lateral sides of the first and the second connecting base, and wherein latching posts are formed on the second cover for locking the latch grooves.

9. The swimming goggles as claimed in claim 8, wherein the first cover includes a first bottom wall and opposing first side walls, wherein an engaging block being a cylinder, and being formed on an edge of the first bottom wall for engaging with the first and the second connecting base, an opening being defined in an edge of the first bottom wall and opposite to the engaging block, a guiding post being formed between the first side walls to retain a head strip, first lock portions being locking grooves, and being respectively defined on bottoms of the first side walls.

10. The swimming goggles as claimed in claim 8, wherein the second cover has a second bottom wall and opposing second side walls, second lock portions being protuberances, and being formed on the second bottom wall for cooperating with the locking grooves to assemble the first cover and the second cover together.

11. The swimming goggles as claimed in claim 8, further comprises a head-strip lock assembled as a level on opposite sides of the first cover, the head-strip lock including a fixing pole, stop strips on both sides of the fixing lever, and a button with a portion extending beyond an assembling hole of the second cover, wherein;

the stop strips extend from an end of the fixing pole and near the opening of the first cover, and the button extends from another end of the fixing pole and opposite the stop strips, and wherein a resilient pole being formed on the second cover for providing return force of the button.

12. Swimming goggles comprising:

a casing frame including an upper frame, a lower frame and a nose support, the upper frame and the lower frame defining closed space, receiving grooves being respectively defined along inner edges of the upper frame and the lower frame for receiving the pad cracks being defined on both sides of the upper frame and the lower frame, the nose support being arranged on a middle of the upper frame and connecting the upper frame and the lower frame thereby dividing the closed space into two slots, the lower frame forming a concave portion, the upper frame forming a gap in a middle of an inner edge thereof;

a pad including an eyeglasses portion and a touch portion, the eyeglasses portion being sandwiched in the receiving grooves;

eyeglasses received in the eyeglasses portion of the pad; and compressing devices mounted on opposite outer sides of the casing frame, each compressing device including a first cover and a second cover which are assembled together and receive a head strip, wherein a first connecting base and a second connecting base unitarily extend from the upper frame and the lower frame and are respectively distributed on opposite sides of the cracks, and wherein positioning grooves and positioning projections are respectively formed near the cracks.

13. Swimming goggles comprising:

a casing frame including an upper frame, a lower frame and a nose support, the upper frame and the lower frame defining closed space, receiving grooves being respectively defined along inner edges of the upper frame and the lower frame for receiving the pad, cracks being defined on both sides of the upper frame and the lower frame, the nose support being arranged on a middle of the upper frame and connecting the upper frame and the lower frame thereby dividing the closed space into two slots, the lower frame forming a concave portion, the upper frame forming a gap in a middle of an inner edge thereof;

a pad including an eyeglasses portion and a touch portion, the eyeglasses portion being sandwiched in the receiving grooves;

eyeglasses received in the eyeglasses portion of the pad; and compressing devices mounted on opposite outer sides of the casing frame, each compressing device including a first cover and a second cover which are assembled together and receive a head strip, wherein the upper frame forms an inject hole communicating with the gap, camber portions being slightly concave respectively on both sides of the inject hole, engaging grooves being respectively formed on both sides of the camber portions, whereby soft material covers the inject hole and the camber portions and clamps the engaging grooves.

* * * * *